(12) United States Patent
Ryan et al.

(10) Patent No.: US 12,023,452 B2
(45) Date of Patent: Jul. 2, 2024

(54) PACKAGE FOR MEDICAL DEVICE FOR ERGONOMIC DEVICE REMOVAL

(71) Applicant: Hollister Incorporated, Libertyville, IL (US)

(72) Inventors: Owen Ryan, Dublin (IE); Pascal Launois, Dublin (IE)

(73) Assignee: Hollister Incorporated, Libertyville, IL (US)

( * ) Notice: Subject to any disclaimer, the term of this patent is extended or adjusted under 35 U.S.C. 154(b) by 0 days.

(21) Appl. No.: 18/305,950

(22) Filed: Apr. 24, 2023

(65) Prior Publication Data

US 2023/0256194 A1    Aug. 17, 2023

Related U.S. Application Data

(62) Division of application No. 16/768,826, filed as application No. PCT/US2018/064063 on Dec. 5, 2018, now Pat. No. 11,666,730.

(60) Provisional application No. 62/596,571, filed on Dec. 8, 2017.

(51) Int. Cl.
   *A61M 25/00* (2006.01)

(52) U.S. Cl.
   CPC ....... *A61M 25/002* (2013.01); *A61M 2209/06* (2013.01)

(58) Field of Classification Search
   CPC .......... B65D 83/0418; B65D 83/0835; B65D 62/22; A61M 2209/06; A61M 25/002; A61M 25/0017

USPC ........ 206/250, 804, 438, 363–369; 211/247, 211/229; 220/793, 791
   See application file for complete search history.

(56) References Cited

U.S. PATENT DOCUMENTS

| | | | |
|---|---|---|---|
| 1,290,750 A | 1/1919 | Huseby | |
| 1,317,501 A | 9/1919 | Huseby | |
| 1,361,842 A | 12/1920 | Evslin | |
| 3,091,327 A | 5/1963 | Lalley | |
| 3,114,455 A | 12/1963 | James | |
| 3,203,545 A | 8/1965 | Grossman | |
| 3,236,588 A * | 2/1966 | Emerson | G01K 13/25 206/804 |
| 3,369,542 A | 2/1968 | Thaidigsman | |
| 3,794,042 A | 2/1974 | De Klotz et al. | |

(Continued)

FOREIGN PATENT DOCUMENTS

| | | |
|---|---|---|
| AT | 369994 B | 2/1983 |
| CN | 2078634 | 6/1991 |

(Continued)

OTHER PUBLICATIONS

Urinary Incontinence Applicance, Aids, and Equipment, R/N.P. Carroll, retrieved on Apr. 3, 2-14 from http://link.springer.com/chapter10.1007/978-1-4471-1461-1_6#, Dec. 31.

(Continued)

*Primary Examiner* — Chun Hoi Cheung
(74) *Attorney, Agent, or Firm* — Cook Alex Ltd.

(57) ABSTRACT

Packages for medical products are disclosed. The packages include a housing and a lid attached to said housing. The lid includes a lifting member that contacts an engagement surface on the medical device whereby opening of said lid allows for removal and presentation of the device for hygienic retrieval by the user.

8 Claims, 4 Drawing Sheets

(56) References Cited

U.S. PATENT DOCUMENTS

| | | |
|---|---|---|
| 3,854,483 A | 12/1974 | Powers |
| 3,867,945 A | 2/1975 | Long |
| 3,894,540 A | 7/1975 | Bonner, Jr. |
| 3,920,023 A | 11/1975 | Dye |
| 3,934,722 A | 1/1976 | Goldberg |
| 4,043,345 A | 8/1977 | Kramann |
| 4,085,841 A | 4/1978 | Matsuyama |
| 4,109,659 A | 8/1978 | Sheridan |
| 4,248,214 A | 2/1981 | Hannah |
| 4,553,959 A | 11/1985 | Hickey |
| 4,684,369 A | 8/1987 | Wildemeersch |
| 4,773,901 A | 9/1988 | Norton |
| 4,935,017 A | 6/1990 | Sylvanowicz |
| 4,956,298 A | 9/1990 | Diekmann |
| 5,012,940 A | 5/1991 | Koehn |
| 5,071,033 A | 12/1991 | Siwek |
| 5,084,036 A | 1/1992 | Rosenbaum |
| 5,133,454 A | 7/1992 | Hammer |
| 5,149,326 A | 9/1992 | Woodgrift |
| 5,217,114 A | 6/1993 | Gadberry |
| 5,225,165 A | 7/1993 | Perlman |
| 5,380,270 A | 1/1995 | Ahmadzadeh |
| 5,413,561 A | 5/1995 | Fischell |
| 5,417,326 A | 5/1995 | Winer |
| 5,582,599 A | 12/1996 | Daneshvar |
| 5,868,265 A | 2/1999 | Kobayashi |
| 5,881,774 A | 3/1999 | Utterberg |
| 5,893,454 A * | 4/1999 | Hermanek ............ A24F 25/02 206/804 |
| 5,919,170 A | 7/1999 | Woessner |
| 6,186,325 B1 | 2/2001 | Schmidt |
| 6,258,078 B1 | 7/2001 | Thilly |
| 6,328,355 B1 | 12/2001 | Bortz |
| 6,439,410 B1 | 8/2002 | Dubach |
| 6,460,712 B2 | 10/2002 | Smith |
| 6,460,726 B1 | 10/2002 | Hierzer |
| 6,585,721 B2 | 7/2003 | Fiore |
| 6,634,498 B2 | 10/2003 | Kayerød |
| 6,726,649 B2 | 4/2004 | Swenson |
| 6,822,253 B1 | 11/2004 | Martin |
| 6,871,753 B2 | 3/2005 | McHutchinson |
| 6,908,013 B2 | 6/2005 | Thomson |
| 6,908,113 B2 | 6/2005 | Chaduc |
| 6,926,708 B1 | 8/2005 | Franks-Farah |
| 6,964,336 B2 | 11/2005 | Harrold |
| 7,120,487 B2 | 10/2006 | Nelson |
| 7,134,575 B2 | 11/2006 | Vogel |
| 7,306,128 B2 | 12/2007 | Eimer |
| 7,311,698 B2 | 12/2007 | Tanghoj |
| 7,353,969 B2 | 4/2008 | McHutchinson |
| 7,438,704 B1 | 10/2008 | Kawashima |
| 7,546,931 B2 | 6/2009 | Giusti |
| 7,571,804 B2 | 8/2009 | Kjellmann Bruun |
| 7,614,514 B2 | 11/2009 | Fuchs |
| 7,624,868 B2 | 12/2009 | Booker |
| 7,699,168 B2 | 4/2010 | Ryan |
| 7,717,284 B2 | 5/2010 | Giusti |
| 7,748,550 B2 | 7/2010 | Cho |
| 7,867,220 B2 | 1/2011 | Tanghoj |
| 7,886,907 B2 | 2/2011 | Murray |
| 7,967,744 B2 | 6/2011 | Kaye |
| 7,992,737 B2 | 8/2011 | Salice |
| 8,137,309 B2 | 3/2012 | Nishtala |
| 8,172,101 B2 | 5/2012 | Giusti |
| 8,181,778 B1 | 5/2012 | van Groningen |
| 8,230,993 B2 | 7/2012 | Tanghoej |
| 8,282,624 B2 | 10/2012 | Tanghoej |
| 8,361,057 B2 | 1/2013 | Tanghoej |
| 8,381,925 B2 | 2/2013 | Skillin |
| 8,398,615 B2 | 3/2013 | Torstensen |
| 8,434,639 B2 | 5/2013 | Markert |
| 8,439,213 B2 | 5/2013 | Goria |
| 8,448,798 B2 | 5/2013 | Groubert |
| 8,491,568 B2 | 7/2013 | Schertiger |
| 8,511,472 B2 | 8/2013 | Dupuis |
| 8,523,843 B2 | 9/2013 | Kavanagh |
| 8,529,549 B2 | 9/2013 | Tanghoj |
| 8,579,115 B2 | 11/2013 | Murphy |
| 8,616,406 B1 | 12/2013 | Sawicki |
| 8,616,407 B2 | 12/2013 | Sawicki |
| 8,733,566 B2 | 5/2014 | Druitt |
| 8,752,722 B2 | 6/2014 | Kuhn |
| 8,863,968 B2 | 10/2014 | Giusti |
| 9,033,149 B2 | 5/2015 | Terry |
| 9,090,386 B2 | 7/2015 | Van Alfen |
| 9,220,866 B2 | 12/2015 | van Groningen |
| 9,334,097 B2 | 5/2016 | Skillin |
| 9,352,318 B2 | 5/2016 | Giusti |
| 9,415,909 B2 | 8/2016 | Druitt |
| 9,422,089 B2 | 8/2016 | Wheeler |
| 9,501,958 B2 | 11/2016 | Pietarinen |
| 9,511,204 B2 | 12/2016 | Tanghøj |
| 9,511,906 B2 | 12/2016 | Van Alfen |
| 9,669,187 B2 | 6/2017 | Tjassens |
| 9,687,629 B1 | 6/2017 | Palmer |
| 9,701,451 B2 | 7/2017 | Skillin |
| 10,857,068 B2 | 12/2020 | Davis |
| 2001/0001443 A1 | 5/2001 | Kayerod |
| 2001/0037954 A1 | 11/2001 | Schmidt |
| 2003/0004496 A1 | 1/2003 | Tanghoj |
| 2003/0060807 A1 | 3/2003 | Tanghoj |
| 2003/0141210 A1 | 7/2003 | Yanke |
| 2004/0016714 A1 | 1/2004 | Wood |
| 2004/0150221 A1 | 8/2004 | Brown |
| 2005/0043715 A1 | 2/2005 | Nestenborg |
| 2005/0067366 A1 | 3/2005 | Dubach |
| 2005/0106339 A1 | 5/2005 | Baker |
| 2005/0106340 A1 | 5/2005 | Baker |
| 2005/0274687 A1 | 12/2005 | McCutchan |
| 2006/0091670 A1 | 5/2006 | Gaynor |
| 2006/0116661 A1 | 6/2006 | Tanghoej |
| 2006/0142737 A1 | 6/2006 | Tanghoj |
| 2006/0180585 A1 | 8/2006 | Cunningham |
| 2007/0034537 A1 | 2/2007 | Fago |
| 2007/0068977 A1 | 3/2007 | Vogel |
| 2008/0033371 A1 | 2/2008 | Updegraff |
| 2008/0183181 A1 | 7/2008 | Treacy |
| 2008/0264961 A1 | 10/2008 | Sawyer |
| 2008/0289984 A1 | 11/2008 | Raven |
| 2008/0319423 A1 | 12/2008 | Tanghoj |
| 2009/0008279 A1 | 1/2009 | Tanghoej |
| 2009/0050253 A1 | 2/2009 | Thomas |
| 2009/0054876 A1 | 2/2009 | Borodulin |
| 2009/0166361 A1 | 7/2009 | Lourenco |
| 2009/0299334 A1 | 12/2009 | Nishtala |
| 2010/0106236 A1 | 4/2010 | Nelson |
| 2010/0211050 A1 | 8/2010 | Luther |
| 2010/0224643 A1 | 9/2010 | Daggett |
| 2010/0256580 A1 | 10/2010 | Faber |
| 2010/0324540 A1 | 12/2010 | Paulen |
| 2011/0060317 A1 | 3/2011 | Frojd |
| 2011/0224653 A1 | 9/2011 | Torstensen |
| 2012/0016318 A1 | 1/2012 | Hoang |
| 2012/0051967 A1 | 3/2012 | Murphy |
| 2012/0165791 A1 | 6/2012 | Lovmar |
| 2012/0179144 A1 | 7/2012 | Carleo |
| 2012/0271281 A1 | 10/2012 | Schertiger |
| 2013/0068767 A1 | 3/2013 | Fraser |
| 2013/0134123 A1 | 5/2013 | Fraser |
| 2013/0150828 A1 | 6/2013 | Conway |
| 2013/0161344 A1 | 6/2013 | Park |
| 2013/0186791 A1 | 7/2013 | Triquigneaux |
| 2013/0218136 A1 | 8/2013 | Tanghoej |
| 2013/0240393 A1 | 9/2013 | Bode |
| 2013/0261608 A1 | 10/2013 | Tanghøj |
| 2013/0289537 A1 | 10/2013 | Schertiger |
| 2013/0292286 A1 | 11/2013 | van Groningen |
| 2013/0299516 A1 | 11/2013 | Dupuis |
| 2013/0327664 A1 | 12/2013 | Tanghøj |
| 2014/0162860 A1 | 6/2014 | Yang |
| 2014/0262860 A1 | 9/2014 | Hagel |
| 2014/0263436 A1 | 9/2014 | Gelov |
| 2014/0360896 A1 | 12/2014 | Torstensen |
| 2016/0016703 A1 | 1/2016 | Muhlemann |

(56) References Cited

U.S. PATENT DOCUMENTS

| | | |
|---|---|---|
| 2016/0023818 A1 | 1/2016 | Gelov |
| 2016/0059999 A1 | 3/2016 | Fraser |
| 2016/0193447 A1 | 7/2016 | Matthiassen |
| 2016/0228872 A1 | 8/2016 | Giusti |
| 2016/0325895 A1 | 11/2016 | Browning, Jr. |
| 2016/0332789 A1 | 11/2016 | Yerecic |
| 2017/0014597 A1 | 1/2017 | Hagel |
| 2017/0080177 A1 | 3/2017 | Tanghoej |
| 2017/0107365 A1 | 4/2017 | Rycroft |
| 2017/0166369 A1 | 6/2017 | Mitten |
| 2017/0173300 A1 | 6/2017 | Hannon |
| 2017/0175428 A1 | 6/2017 | Quinn |
| 2017/0326334 A1 | 11/2017 | Terry |

FOREIGN PATENT DOCUMENTS

| | | |
|---|---|---|
| CN | 2340720 Y | 9/1999 |
| DE | 20117438 U1 | 3/2002 |
| DE | 10213411 A1 | 10/2003 |
| DE | 20317135 U1 | 1/2004 |
| DE | 202005008071 U1 | 7/2005 |
| DE | 102004013712 B3 | 8/2005 |
| DE | 202005009946 U1 | 9/2005 |
| DE | 202006013663 U1 | 11/2006 |
| DE | 202010006267 U1 | 11/2010 |
| DE | 202010007433 U1 | 6/2011 |
| DE | 202011107025 U1 | 1/2013 |
| DE | 202011107059 U1 | 1/2013 |
| DE | 102013014483 A1 | 6/2014 |
| DE | 202017101126 U1 | 3/2017 |
| DE | 102016205834 B3 | 5/2017 |
| DK | 173714 B1 | 7/2001 |
| EP | 0041487 A1 | 12/1981 |
| EP | 0134630 A1 | 3/1985 |
| EP | 0781572 A2 | 7/1997 |
| EP | 0812287 A1 | 12/1997 |
| EP | 0861639 A2 | 9/1998 |
| EP | 0910425 A1 | 4/1999 |
| EP | 0923398 A1 | 6/1999 |
| EP | 0933304 A1 | 8/1999 |
| EP | 0996542 A1 | 5/2000 |
| EP | 1023882 A1 | 8/2000 |
| EP | 1086024 A1 | 3/2001 |
| EP | 1278679 A1 | 1/2003 |
| EP | 1317382 A1 | 6/2003 |
| EP | 1334039 A1 | 8/2003 |
| EP | 1392575 A1 | 3/2004 |
| EP | 1409369 A1 | 4/2004 |
| EP | 1466645 A2 | 10/2004 |
| EP | 1487712 A2 | 12/2004 |
| EP | 1593710 A1 | 11/2005 |
| EP | 1607344 A1 | 12/2005 |
| EP | 1615960 A1 | 1/2006 |
| EP | 1634554 A2 | 3/2006 |
| EP | 1638856 A1 | 3/2006 |
| EP | 1671663 A1 | 6/2006 |
| EP | 1696990 A1 | 9/2006 |
| EP | 1720772 A1 | 11/2006 |
| EP | 1858575 A1 | 11/2007 |
| EP | 1863719 A2 | 12/2007 |
| EP | 1799574 B1 | 1/2008 |
| EP | 1878461 A1 | 1/2008 |
| EP | 1897579 A1 | 3/2008 |
| EP | 1897580 A1 | 3/2008 |
| EP | 1963195 A2 | 9/2008 |
| EP | 1966058 A1 | 9/2008 |
| EP | 1979032 A1 | 10/2008 |
| EP | 1982741 A2 | 10/2008 |
| EP | 1986921 A1 | 11/2008 |
| EP | 2035292 A2 | 3/2009 |
| EP | 2042211 A1 | 4/2009 |
| EP | 2044963 A1 | 4/2009 |
| EP | 2060296 A1 | 5/2009 |
| EP | 2072075 A1 | 6/2009 |
| EP | 2106821 A1 | 10/2009 |
| EP | 2242696 A1 | 10/2010 |
| EP | 2250102 A1 | 11/2010 |
| EP | 2251454 A2 | 11/2010 |
| EP | 2292294 A1 | 3/2011 |
| EP | 2295108 A1 | 3/2011 |
| EP | 2308543 A1 | 4/2011 |
| EP | 2450076 A1 | 5/2012 |
| EP | 2468319 A1 | 6/2012 |
| EP | 2325100 B1 | 8/2012 |
| EP | 2504054 A1 | 10/2012 |
| EP | 2515985 A1 | 10/2012 |
| EP | 2576374 A1 | 4/2013 |
| EP | 2596831 A2 | 5/2013 |
| EP | 2617316 A2 | 7/2013 |
| EP | 2638927 A2 | 9/2013 |
| EP | 2682069 A1 | 1/2014 |
| EP | 2686054 A1 | 1/2014 |
| EP | 2750748 A1 | 7/2014 |
| EP | 2774648 A1 | 9/2014 |
| EP | 2782842 A1 | 10/2014 |
| EP | 2785409 A1 | 10/2014 |
| EP | 2823845 A1 | 1/2015 |
| EP | 3033279 A1 | 6/2016 |
| EP | 3038075 A2 | 6/2016 |
| EP | 3113922 A1 | 1/2017 |
| EP | 2605977 B1 | 5/2017 |
| EP | 3210909 A1 | 8/2017 |
| EP | 3298620 A1 | 3/2018 |
| FR | 2717676 A1 | 9/1995 |
| GB | 2031735 A | 4/1980 |
| GB | 2033231 A | 5/1980 |
| GB | 2322079 A | 8/1998 |
| JP | 2011025473 A | 2/2011 |
| KR | 20110101674 A | 9/2011 |
| PT | 2216064 T | 9/2016 |
| SE | 514121 C2 | 1/2001 |
| WO | 9608219 A1 | 3/1996 |
| WO | 9726937 A1 | 7/1997 |
| WO | 9741811 A1 | 11/1997 |
| WO | 9811932 A1 | 3/1998 |
| WO | 9819729 A1 | 5/1998 |
| WO | 9930761 A1 | 6/1999 |
| WO | 9942155 A2 | 8/1999 |
| WO | 0016843 A1 | 3/2000 |
| WO | 0030575 A1 | 6/2000 |
| WO | 0047494 A1 | 8/2000 |
| WO | 0143807 A1 | 6/2001 |
| WO | 0160255 A1 | 8/2001 |
| WO | 02060361 A2 | 8/2002 |
| WO | 02080843 A2 | 10/2002 |
| WO | 03001994 A1 | 1/2003 |
| WO | 03008028 A2 | 1/2003 |
| WO | 03008029 A2 | 1/2003 |
| WO | 03022561 A1 | 3/2003 |
| WO | 03045487 A2 | 6/2003 |
| WO | 03061732 A2 | 7/2003 |
| WO | 03092779 A1 | 11/2003 |
| WO | 03097237 A2 | 11/2003 |
| WO | 2004021890 A1 | 3/2004 |
| WO | 2004032750 A1 | 4/2004 |
| WO | 2004035123 A1 | 4/2004 |
| WO | 2004050155 A1 | 6/2004 |
| WO | 2004054446 A1 | 7/2004 |
| WO | 2004054653 A1 | 7/2004 |
| WO | 2004056414 A1 | 7/2004 |
| WO | 2004089454 A1 | 10/2004 |
| WO | 2004103153 A2 | 12/2004 |
| WO | 2005014055 A2 | 2/2005 |
| WO | 2005056414 A1 | 6/2005 |
| WO | 2005092418 A1 | 10/2005 |
| WO | 2006005349 A2 | 1/2006 |
| WO | 2006017439 A2 | 2/2006 |
| WO | 2006044249 A2 | 4/2006 |
| WO | 2006044621 A2 | 4/2006 |
| WO | 2006045809 A1 | 5/2006 |
| WO | 2006092150 A1 | 9/2006 |
| WO | 2006121183 A1 | 11/2006 |
| WO | 2007005851 A2 | 1/2007 |
| WO | 2007022223 A2 | 2/2007 |

(56) References Cited

FOREIGN PATENT DOCUMENTS

| | | |
|---|---|---|
| WO | 2007038988 A1 | 4/2007 |
| WO | 2007050685 A2 | 5/2007 |
| WO | 2007081264 A1 | 7/2007 |
| WO | 2007082540 A1 | 7/2007 |
| WO | 2007106356 A2 | 9/2007 |
| WO | 2007106431 A2 | 9/2007 |
| WO | 2007111891 A2 | 10/2007 |
| WO | 2007121137 A2 | 10/2007 |
| WO | 2008024136 A1 | 2/2008 |
| WO | 2008030999 A2 | 3/2008 |
| WO | 2008039910 A2 | 4/2008 |
| WO | 2008089081 A1 | 7/2008 |
| WO | 2008090551 A2 | 7/2008 |
| WO | 2008137353 A1 | 11/2008 |
| WO | 2009010975 A1 | 1/2009 |
| WO | 2009017541 A1 | 2/2009 |
| WO | 2009068043 A2 | 6/2009 |
| WO | 2009139878 A1 | 11/2009 |
| WO | 2010006620 A1 | 1/2010 |
| WO | 2010130261 A1 | 11/2010 |
| WO | 2011011023 A1 | 1/2011 |
| WO | 2011019359 A1 | 2/2011 |
| WO | 2011026929 A1 | 3/2011 |
| WO | 2011034911 A1 | 3/2011 |
| WO | 2011079129 A1 | 6/2011 |
| WO | 2011109393 A1 | 9/2011 |
| WO | 2011147803 A1 | 12/2011 |
| WO | 2012006629 A2 | 1/2012 |
| WO | 2012013662 A1 | 2/2012 |
| WO | 2012016179 A1 | 2/2012 |
| WO | 2012016570 A2 | 2/2012 |
| WO | 2012016571 A2 | 2/2012 |
| WO | 2012060699 A1 | 5/2012 |
| WO | 2012079590 A1 | 6/2012 |
| WO | 2012085107 A2 | 6/2012 |
| WO | 2012110755 A2 | 8/2012 |
| WO | 2012134804 A1 | 10/2012 |
| WO | 2012154946 A1 | 11/2012 |
| WO | 2012156478 A1 | 11/2012 |
| WO | 2012166045 A1 | 12/2012 |
| WO | 2012166967 A1 | 12/2012 |
| WO | 2013029620 A1 | 3/2013 |
| WO | 2013029621 A1 | 3/2013 |
| WO | 2013029622 A1 | 3/2013 |
| WO | 2013075725 A1 | 5/2013 |
| WO | 2013083137 A1 | 6/2013 |
| WO | 2013098190 A1 | 7/2013 |
| WO | 2013105091 A1 | 7/2013 |
| WO | 2014062223 A1 | 4/2014 |
| WO | 2014062225 A1 | 4/2014 |
| WO | 2014063711 A1 | 5/2014 |
| WO | 2014074141 A1 | 5/2014 |
| WO | 2014074147 A1 | 5/2014 |
| WO | 2014081859 A1 | 5/2014 |
| WO | 2014085597 A1 | 6/2014 |
| WO | 2014093056 A1 | 6/2014 |
| WO | 2014139767 A2 | 9/2014 |
| WO | 2014140328 A1 | 9/2014 |
| WO | 2014142895 A1 | 9/2014 |
| WO | 2014142917 A1 | 9/2014 |
| WO | 2014142923 A1 | 9/2014 |
| WO | 2014142930 A1 | 9/2014 |
| WO | 2014144714 A1 | 9/2014 |
| WO | 2014145211 A2 | 9/2014 |
| WO | 2014147620 A1 | 9/2014 |
| WO | 2014149276 A1 | 9/2014 |
| WO | 2014159869 A2 | 10/2014 |
| WO | 2014165046 A1 | 10/2014 |
| WO | 2014176486 A1 | 10/2014 |
| WO | 2014176867 A1 | 11/2014 |
| WO | 2015065725 A1 | 5/2015 |
| WO | 2015066673 A1 | 5/2015 |
| WO | 2015075841 A1 | 5/2015 |
| WO | 2015120119 A1 | 8/2015 |
| WO | 2015184365 A1 | 12/2015 |
| WO | 2016044379 A2 | 3/2016 |
| WO | 2016094606 A1 | 6/2016 |
| WO | 2017024106 A1 | 2/2017 |
| WO | 2017174715 A1 | 10/2017 |
| WO | 2017185029 A1 | 10/2017 |
| WO | 2017185052 A1 | 10/2017 |

OTHER PUBLICATIONS

"Total Body Relief and Hygeine for Travel, home bath and life's less comfortable moments", http://www.biorelief.com/blog/self-cath-fits-in-your-pocket/, dated Apr. 19, 2014.

International Search Report and Written Opinion, issued in connection with International Application No. PCT/US2017/028979 dated Aug. 25, 2017.

International Search Report, issued in connection with International Application No. PCT/US2014/053573 dated Feb. 24, 2015.

International Search Report, issued in connection with International Application No. PCT/US2015/033344 dated Sep. 11, 2015.

International Search Report and Written Opinion, issued in connection with International Application No. PCT/US2018/018965 dated Sep. 24, 2018.

International Search Report and Written Opinion, issued in connection with International Application No. PCT/US2017/028937 dated Aug. 21, 2017.

International Search Report and Written Opinion for International Application No. PCT/US2018/064063, dated Sep. 4, 2019.

* cited by examiner

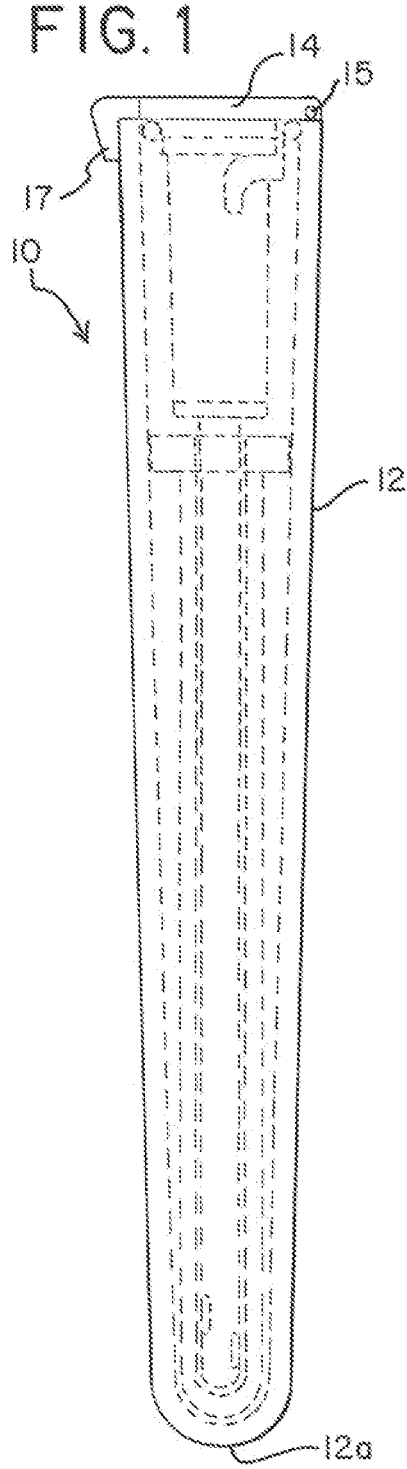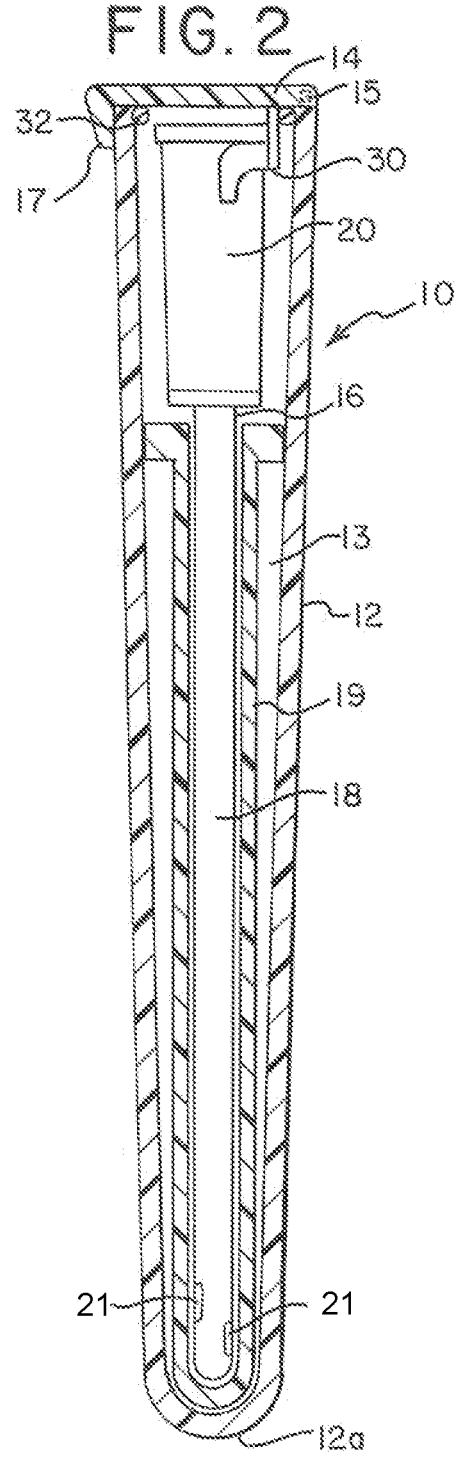

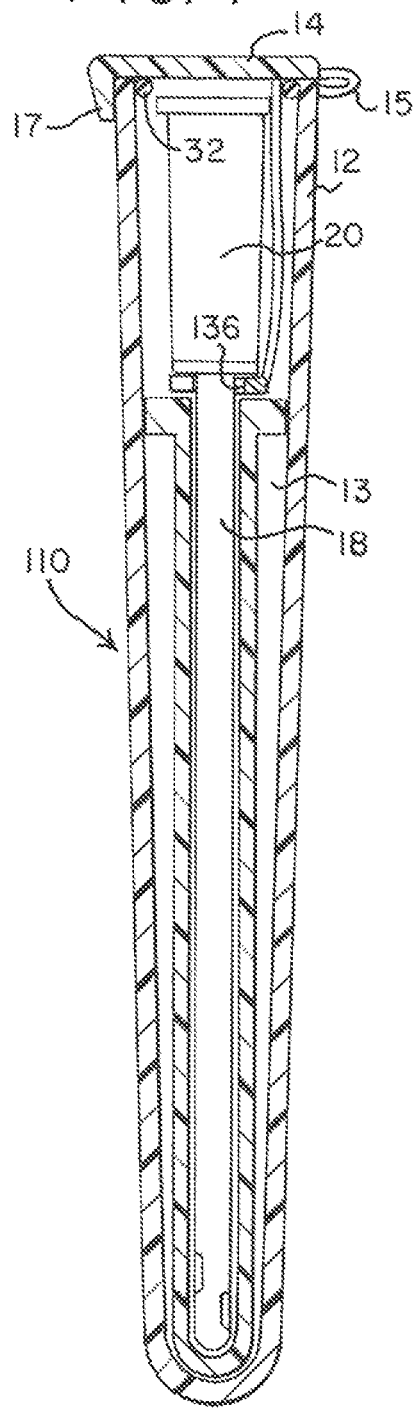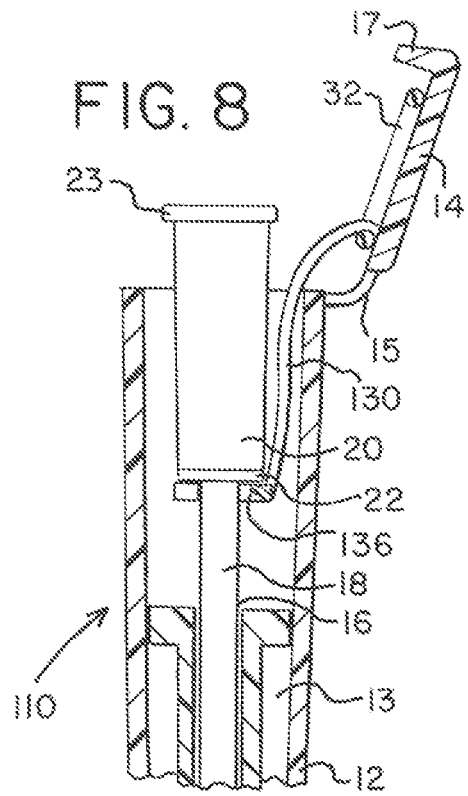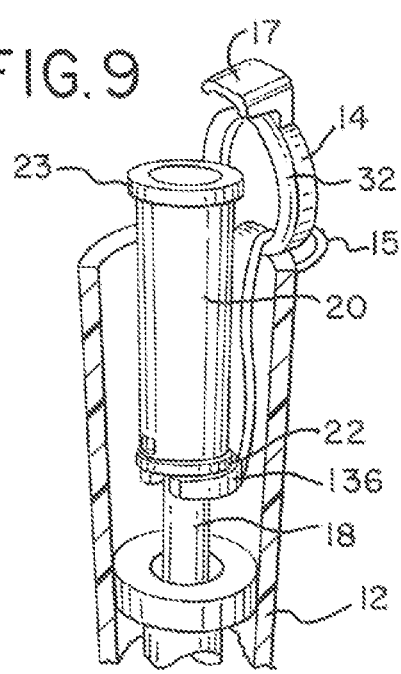

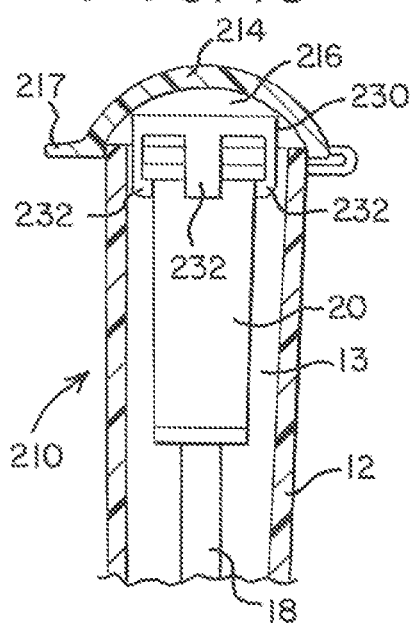
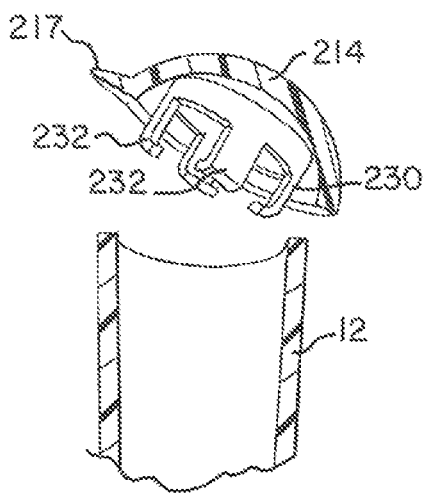
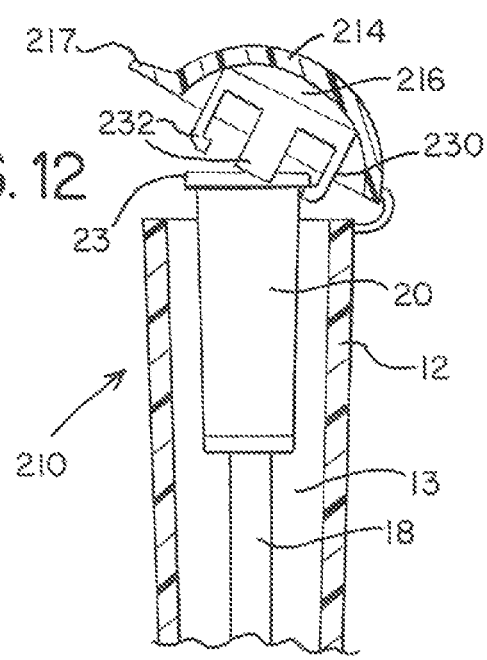

PACKAGE FOR MEDICAL DEVICE FOR ERGONOMIC DEVICE REMOVAL

CROSS-REFERENCE TO RELATED APPLICATIONS

This is a Divisional application of U.S. application Ser. No. 16/768,826, filed on Jun. 1, 2020, which is the U.S. National Stage Application of International Application No. PCT/US2018/064063, filed on Dec. 5, 2018, which claims the benefit of and priority to U.S. Provisional Patent Application Ser. No. 62/596,571, filed Dec. 8, 2017, all of which are hereby incorporated by reference herein in their entireties.

FIELD OF THE DISCLOSURE

The present disclosure is directed to packages for medical products. More particularly, the present disclosure is directed to packages for medical devices that allow for ergonomic presentation and removal of the device from the package. Even more particularly, the present disclosure is directed to packages for urinary catheters such as intermittent urinary catheters, whereby opening of the package presents the non-insertable portion of the catheter such that it can be easily removed from the package by the user.

BACKGROUND

Intermittent catheters are widely used by individuals who suffer from compromised dexterity caused by injury to the spinal cord. The difficulties associated with manipulating and opening the package, holding the catheter and accessing the catheter in an easy and sterile manner has led catheter manufacturers to consider ways whereby the catheter package can be easily opened and, upon the opening of the package, present the catheter such that the user can easily retrieve the catheter from the package.

One example of a catheter package that provides for presentation of and access to the catheter upon opening of the package is disclosed in EP 2 686 054 B1. The catheter and catheter package described in EP 2 686 054 B1 includes extracting means coupled to the catheter at one end and a peel away tab of the package at its other end. When the peel-off tab is opened, the extracting member, which is shown as a strip of material, partially pulls the catheter out of the package and into the opening of the package.

In a second embodiment of the catheter package described in EP 2 686 054 B1, the package includes a cap which seals the open end of the package. The extraction means in this embodiment is also provided in the form of a flexible strip, one end of which is attached to the cap and the other end is attached to an insertion aid of the catheter assembly. When the tab on the cap is moved and the package opened, the extracting means partially lifts the catheter out of the package.

The present disclosure provides further improvements in the packaging of catheters or, for that matter, any medical device that is to be accessed by the user in a way that presents the device for easy and sterile removal from the package.

SUMMARY

In one aspect, the present disclosure is directed to a package for a medical device. The device includes an elongated housing having a closed proximal end and an open distal end. An openable lid is attached to the housing for sealing the open distal end of the housing. The lid includes a lifting member that is movable with the lid during opening of the package.

In another aspect, the present disclosure is directed to a catheter product including a package with an elongated housing having a closed proximal end and an open distal. An openable lid is attached to the housing for sealing the open distal end. The lid includes a lifting member that is movable with the lid during opening of the package. The product also includes a catheter having a proximal insertable catheter tube and a distal gripping member or funnel. The gripping member includes an engagement surface that is in contact with the lifting member of the lid. Opening of the package lid partially lifts the catheter out of the package and presents the catheter for hygienic retrieval of the catheter by the user.

BRIEF DESCRIPTION OF THE DRAWINGS

FIG. 1 is a plan view of a package for a medical device;

FIG. 2 is a cross-sectional view of the package of FIG. 1 with the medical device disposed therein;

FIG. 7 is a cross-sectional view of an alternative embodiment of a package for a medical device with the medical device disposed therein;

FIG. 8 is a partial, cross-sectional view of the package of FIG. 7 with medical device therein with the lid of the package in an open position;

FIG. 9 is a partial, cross-sectional perspective view of the package of FIG. 7 with medical device therein with the lid of the package in an open position;

FIG. 10 is a partial view of yet another embodiment of a package for a medical device in accordance with the present disclosure with the lid in the closed position;

FIG. 11 is perspective view of the lid of the package of FIG. 10; and

FIG. 12 is a partial, cross-sectional view of the package and product of FIG. 11 with the lid in the open position.

DETAILED DESCRIPTION OF THE EMBODIMENTS

The disclosure that follows describes the invention in the context of a urinary catheter and a package for such catheter. However, it will be understood that the invention is not limited to urinary catheters or even catheters. The invention(s) disclosed herein are applicable to any medical device and package for such device wherein the opening of the package presents the device to the user for easy and sterile retrieval from the package.

Turning now to the Figures, FIGS. 1-2 show a package 10 for a medical device in accordance with the present disclosure. Package 10 includes a housing 12 for receiving a medical device, such as a catheter. Housing 12 may typically be elongated, having walls that define an interior chamber 13 for housing the catheter. Housing 12 may be generally cylindrically shaped or have a substantially tubular profile as shown herein and/or, for example, in International Publication No. WO 2017/185052, the contents of which are incorporated herein by reference. Alternatively, housing 12 may have a more squared cylindrical shape with beveled edges, as shown and described in U.S. Patent Publication 2017/0173300.

Typically, housing 12 may be made of molded plastic to provide a rigid or substantially rigid case for the catheter or other medical device. In one embodiment, housing 12 may be molded from a polymeric material such as polypropylene. Housing 12 may be made from a unitary or multilayer polymeric material.

Figure 4:
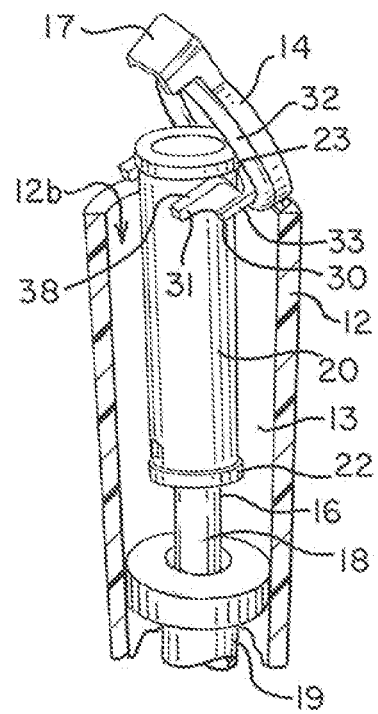
FIG. 4 is a partial, cross-sectional view of the package of FIG. 3 with medical device therein with the lid of the package in a partially open position.
Figure 5:
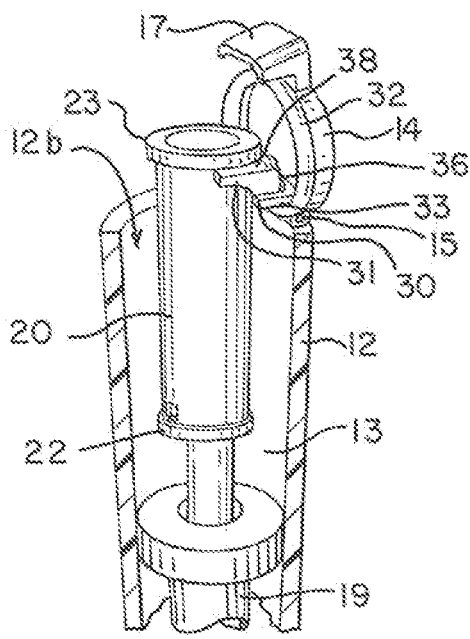
FIG. 5 is a partial, cross-sectional view of the package of FIG. 3 with medical device therein with the lid of the package in a fully open position.
Figure 6:
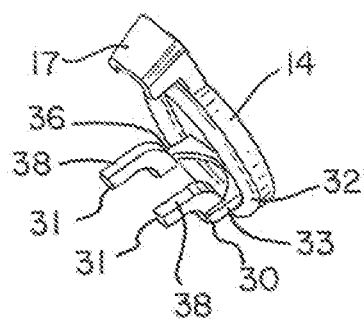
FIG. 6 is a perspective view of the lid of the package of FIGS. 1 and 2.

Housing 12 has a closed sealed proximal end 12a and an openable distal end 12b (FIGS. 4-5). The terms "distal" and "proximal" are used throughout this disclosure. When used in the context of a catheter having a catheter tube that is inserted into the body of the user, the term "proximal" is used to refer to that end or portion of the catheter that during use is closer in proximity to the user's body and/or initially enters the user's body upon insertion. The term "distal" is used to refer to an end or portion of the catheter (or catheter tube) that is opposite the proximal end or portion and is typically further away from the user's body. For the sake of consistency, when the terms "distal" and "proximal" are used in the context of a housing or member that holds the catheter or carries the catheter tube, and which are not intended for introduction into the user's body, a proximal end or proximal portion is that end or portion closer to the proximal end of the catheter and/or catheter tube when the catheter tube is housed in or carried by the member, while the distal end or portion is located opposite to such proximal end or portion.

As further shown in FIGS. 1-6, package 10 and more specifically housing 12 will include an openable cap or lid 14. Lid 14 seals distal open end 12b until opened by the user. In one embodiment, lid 14 may be a flat or substantially flat cap hingedly attached to housing 12 by hinge 15. Hinge 15 may be of any type that is commonly used, including a living hinge that can alternately be moved between open and closed positions. Lid 14 may also include a tab 17 located opposite hinge 15 for easy manipulation by the user. By pushing on tab 17, lid 14 is opened to allow access to the medical device housed inside housing 12. As shown in FIGS. 1-6, lid 14 may further include a sealing element such as O-ring 32 around the perimeter of lid 14 to provide a liquid-tight seal between the lid and the housing. Further examples of suitable hinges and sealing elements that may be used in package 10 are also disclosed in International Publication No. WO 2017/185052, previously incorporated by reference.

As set forth above, the medical device within housing 12 may be any device that is intended for retrieval and immediate use by the user. In a preferred embodiment, the medical device is an intermittent catheter, such as catheter 16 shown in FIGS. 1-6 within housing 12. Optionally, housing 12 may further include a hydration liner 19 within interior chamber 13. Liner 19 may receive the insertable portion of catheter 16. Such liners are described in greater detail in U.S. Patent Publication 2017/0173300 and International Publication No. WO 2017/185052, both of which are incorporated herein by reference.

Catheter 16 includes catheter tube 18 made of a polymeric material such a polyvinyl chloride (PVC), which is typically made hydrophilic by coating tube 18 with a lubricious coating. Catheter tube 18 further includes one or more eyelets 21 at the proximal end of tube 18 to receive urine from the urinary canal of the user. Catheter tube 18 is insertable into the urethra of a patient.

Catheter 16 includes a funnel 20 at its distal end. Typically, funnel 20 has a hollow interior that is in flow of communication with the lumen of catheter tube 18. Funnel 20 provides an outlet for urine as it flows out of the urinary canal through the catheter tube 18. In some embodiments, a urine collection bag may be attached to the distal end of funnel 20.

As shown in the Figures, funnel 20 may further include one or more flanges 22 and 23 at the distal and proximal ends of funnel 20, respectively. Funnel 20 not only serves as a fluid outlet for urine, it also provides and serves as a gripping member that can be held and manipulated by the user when removing a catheter 16 from housing 12, and when inserting catheter tube 18 into the urethra. Thus, funnel 20 will typically include a textured outer surface to enhance gripping by the user. Examples of such texturing are shown and described in International Publication No. WO 2017/185052, previously incorporated by reference. By gripping catheter 16 at the funnel 20, user contact with the insertable portion of the catheter, namely catheter tube 18 is avoided.

Figure 3:
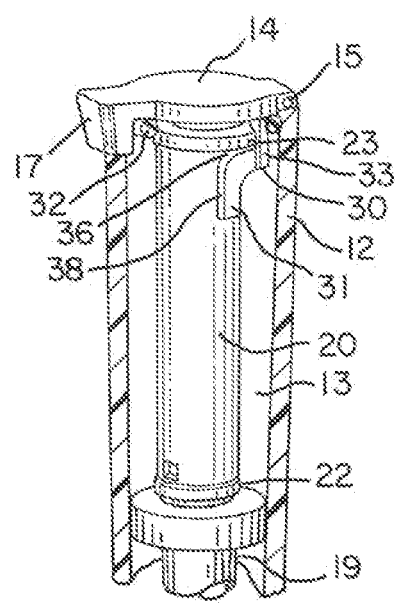
FIG. 3 is a partial, cross-sectional view of the package with medical device of FIGS. 1 and 2 therein with the lid of the package in a closed position.

As shown in the FIGS. 3-5 and further described herein, catheter package 10 provides for ready accessibility of the catheter funnel 20, allowing for easy removal by the user upon opening lid 14. It will be appreciated, that prior to use, catheter 16 remains completely concealed within package 10, as generally shown in FIG. 3. As further shown in the Figures, flange 23 at the distal end of funnel 20 remains below opening 12b of housing 12. It would be difficult for a user, particularly one of limited dexterity, to insert his/her fingers into the interior chamber 13 of housing 12 to remove catheter 16, nor would this be desired from the standpoint of sterility and avoiding contamination of the catheter tube. Accordingly, as shown in FIGS. 1-6, in one embodiment, catheter package includes one or more lifting members 30 that contact funnel and lift catheter 16 as lid 14 is being opened. As shown in FIGS. 1-6, lifting members 30 may include lifting arms 31 carried by support arms 33. Support arms 33 preferably depend downwardly in the direction of chamber 13 when lid 14 is in its closed position. As best seen in FIG. 3, support arms 33 are preferably attached to and/or are integral with the underside of lid 14. Lifting arms 31 are preferably attached to the proximal ends of support arms 33. In one embodiment, lifting arms 31 are L-shaped members including a first contacting surface 36 that extends substantially perpendicularly from support arm 33, and a second contacting surface 38 that extends perpendicularly from first contacting surface 36, thus forming the preferable L-shape of lifting arms 31.

As shown in FIG. 3, when lid 14 is in its closed position, first contacting surface 36 of lifting arm 31 is preferably located below and in contact with flange 23 of funnel 20. Lifting member 30 is carried by lid 14 and attached to the underside of lid 14 near hinge 15 joined to lid 14. As shown in FIGS. 4-5, as the user flips open lid 14, lifting arms 31 pivot with lid 14 as it moves from the closed to a partially open and then a fully open position. First contacting surface 36 of lifting arms 31 (which is initially in contact with flange 23) lifts funnel 20 out of chamber 13. As the first contacting surface 36 of lifting arms 31 moves with lid 14 out of contact with flange 23, second contacting surface 38 of lifting arms 31, comes into contact with flange 23, further lifting funnel 20 out from the interior chamber 13 of the package 10, as shown in FIGS. 4-5. Once lid 14 is open, gripping member/ funnel 20 has been sufficiently removed from the housing 12 and is presented and accessible to the user for removal of catheter 16.

FIGS. 7-9 show an alternative embodiment of the medical device package 110. In many respects, the housing and catheter are identical to the structure and function previously described in connection with the embodiment of FIGS. 1-6. Accordingly, identical reference numerals are used for such identical or similar structures. Rather than using lifting arms to lift funnel 20 out from the chamber 13, in the embodiment of FIGS. 7-9, an elongated, preferably single connector 130 may be used to lift funnel 20 out from chamber 13. Connector 130 may be attached to the underside of lid 14. Specifically, where connector 130 is a flexible strip or a strap of a polymeric or other material, one end 132 of connector of 130 is attached to the underside of lid 14. The other end 134 of connector 130 terminates in and/or is attached to an engagement member 136. As shown in FIGS. 7-8, in one embodiment, engagement member 136 may be in the form of a ring or collar. In one embodiment, collar 136 is located below lower funnel flange 22. The length of connector 130 may be selected such that when lid 14 moves from its closed position to its fully opened position, funnel 20 is fully presented and accessible outside of housing 12.

FIGS. 10-12 depict yet another embodiment of a medical device package 210 in accordance with the present disclosure. As seen in FIGS. 10-12, lid 214 is a bulbous or otherwise nonflat closure defining a hollow region 216 within lid 214. Extending from the underside of lid 214 into hollow interior region 216 and further into cavity 13 is a lifting member 230 that includes one or more claws or barbs 232 that extend downwardly from lifting member 230. In the embodiment of FIGS. 10-12, there are four claws/barbs 232 shown, but it will be understood that any number of claws/barbs 232 may be provided. It is preferred that the claws or barbs 232 be equally spaced from one another around the perimeter of lifting member 230.

During opening of lid 214 (by applying upward pressure to tab 217), claws/barbs 232 which are initially engaged to the underside of flange 23, lift funnel 20 out from the cavity 13. As lid 214 is flipped open, claws/barbs 232 pull catheter 16 out from the interior chamber 13 and present funnel 20 for removal by the user.

It should be understood that various changes and modifications to the described embodiments may be made without departing from the spirit and scope of invention(s) disclosed herein.

The invention claimed is:

1. A catheter product comprising:
    a) a package comprising an elongated housing having a closed proximal end and an open distal end and an openable lid attached to said housing for sealing the open distal end of said housing, said lid comprising a lifting member that is movable with said lid during opening of said package, wherein said lifting member comprises a connector attached to an engagement member, wherein the engagement member is a collar that includes an engagement member proximal surface facing the closed proximal end of the housing and an engagement member distal surface; and
    b) a catheter comprising a proximal insertable catheter tube and a distal gripping member, said gripping member comprising a proximal end and a distal end, a flange located at said proximal end of the gripping member, wherein the flange comprises a bottom surface including an engagement surface in contact with said engagement member distal surface.

2. The catheter product of claim 1 wherein said lid comprises a top surface and an underside and wherein a distal end of the connector is attached to the underside of said lid.

3. The catheter product of claim 2 wherein said top surface of said lid is flat.

4. The catheter product of claim 2 wherein said lid comprises a sealing element located on the underside of said lid.

5. The catheter product of claim 1 wherein the connector comprises a proximal end attached to the engagement member.

6. The catheter product of claim 1 wherein said gripping member comprises a cylindrical member.

7. The catheter product of claim 1 wherein said lid comprises a tab.

8. The catheter product of claim 7 further comprising a hinge joining said lid and said housing, wherein said hinge is spaced from said tab at a location opposite said tab.

* * * * *